United States Patent [19]

Bergstrom et al.

[11] Patent Number: 5,132,320
[45] Date of Patent: Jul. 21, 1992

[54] SQUALENE SYNTHETASE INHIBITORS

[75] Inventors: James D. Bergstrom, Neshanic; Otto D. Hensens, Red Bank; Claude Dufresne, Edison; Leeyuan Huang, Watchung; Janet C. Onishi, Mountainside; Deborah L. Zink, Manalapan, all of N.J.

[73] Assignee: Merck & Co., Inc., Rahway, N.J.

[21] Appl. No.: 496,734

[22] Filed: Mar. 21, 1990

[51] Int. Cl.$^5$ .................. A61K 31/335; C07D 319/08
[52] U.S. Cl. ..................................... 514/452; 549/363
[58] Field of Search ........................ 549/363; 514/452

[56] References Cited

U.S. PATENT DOCUMENTS 4,871,721 10/1989 Biller ..................................... 514/102

FOREIGN PATENT DOCUMENTS

0405864A2 1/1991 European Pat. Off. .

OTHER PUBLICATIONS

S. A. Biller et al, *J. Med. Chem.*, 31, 1869 (1988).

C. D. Poulter et al, *J. Am. Chem. Soc.*, 111, 3734 (1989).

E. J. Corey et al, *J. Am. Chem. Soc.*, 98, 1291 (1976).

Primary Examiner—Nicky Chan
Attorney, Agent, or Firm—Joseph DiPrima; Melvin Winokur

[57] ABSTRACT

This invention relates to compounds of structural formula (I):

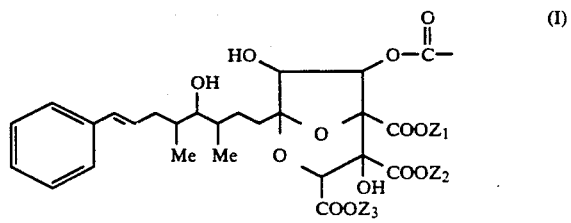

$-(CH_2)_4-CH=CH-(CH_2)_4-CH=CH-CH_3$ which are squalene synthetase inhibitors and thus useful as cholesterol lowering agents.

14 Claims, 2 Drawing Sheets

FIG. 1

FIG.2

SQUALENE SYNTHETASE INHIBITORS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR ® (lovastatin), now commercially available. is one of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analog containing compounds such as those described in P. Ortiz de Montellano et al, J. Med Chem. 20, 243 (1977) and E. J. Corey and R. Volante, J. Am. Chem. Soc., 98, 1291 (1976). S. Biller (U.S. Pat. No. 4,871,721) describes isoprenoid (phosphinylmethyl)phosphonates as inhibitors of squalene synthetase.

The present invention provides nonphosphorus containing inhibitors of squalene synthetase.

DETAILED DESCRIPTION OF THE INVENTION

The present invention is directed to novel compounds of structural formula (I) which are squalene synthetase inhibitors:

wherein
$Z_1$, $Z_2$ and $Z_3$ are each independently selected from;
a) H;
b) $C_{1-5}$alkyl;
c) $C_{1-5}$alkyl substituted with a member of the group consisting of:
  i) phenyl,
  ii) phenyl substituted with methyl, methoxy, halogen (Cl, Br, F, I) or hydroxy; or a pharmaceutically acceptable salt of a compound of of formula (I) in which at least one of $Z_1$, $Z_2$ and $Z_3$ is hydrogen.

In one embodiment of the present invention are those compounds of formula (I) wherein the relative stereochemical configuration of the 2,8-dioxabicyclo[3.2.1]octane ring is as shown below:

Throughout this specification and claims where stereochemistry is described for the dioxabicyclo[3.2.1]octane ring the configuration implied is relative. The actual configuration may be as shown or that of its enantiomer.

Further illustrating this embodiment are those compounds of structural formula (I) wherein the relative configuration at positions 3, 6 and 7 is as shown below:

In one class of this embodiment are those compounds of structure (I) wherein the relative configuration at the 4-position is as shown below:

Exemplifying this class is the compound wherein $Z_1$, $Z_2$ and $Z_3$ are each hydrogen or a pharmaceutically acceptable salt thereof. The compound wherein $Z_1$, $Z_2$ and $Z_3$ are each hydrogen is hereafter referred to as Compound A.

Further illustrating this class are those compounds in which one or more of $Z_1$, $Z_2$ or $Z_3$ is $C_{1-5}$alkyl or $C_{1-5}$alkyl substituted with phenyl or substituted phenyl wherein the substituent is methyl, methoxy, halogen or hydroxy. In a specific illustration, $Z_1$, $Z_2$ and $Z_3$ are each methyl. This compound is hereafter referred to as Compound B.

The double bonds within the $C_{14}$ dienoic side chain may both be in a trans configuration or one of the two may be in a cis configuration or both may be in a cis configuration.

The compounds of formula (I) are prepared in an aerobic fermentation procedure employing a novel culture, MF5447, identified as *Sporormiella intermedia*. Compounds of formula (I) may also be obtained in a fermentation procedure employing a novel culture MF5466, identified as a bitunicate ascomycete. Although the use of these organisms is specifically described herein, other organisms of the genera Sporormiella and Preussia including mutants of the above described organisms are also capable of producing compounds of this invention.

The culture MF5447 is that of a coprophilous fungus, *Sporormiella intermedia*, isolated from cottontail rabbit dung (Arizona). This culture has been deposited with the American Type Culture Collection at 12301 Parklawn Drive, Rockville, Md. 20852 as ATCC 20985. Culture MF5466 is that of a coprophilous fungus, a bitunicate ascomycete, isolated from big horn sheep dung (Tucson, Ariz.). This culture has been deposited as ATCC 20989.

The culture MF5447, identified as *Sporormiella intermedia* exhibits the following morphological features.

Pseudothecia maturing in 4-5 weeks on either inoculted deer dung or on oatmeal agar (Difco) at 25° C. in continous fluorescent light. Pseudothecia on surface of inoculated deer dung single to densely gregarious, embedded, with upper 10-50% protruding above the surface, 200-300 μm in diameter, globose to subglobose, nonostiolate, glabrous, dull, uniformly black. Peridium thin, 1-2 cells thick, a textura angularis. Peridial cells isodiametric, 4-8 μm in diameter, gray to dark olivaceous gray in KOH.

Asci abundant, arising from a common basal area, bitunicate, 8-spored, cylindrical, straight to slightly curved, with broad rounded apex, 120-180 μm ×20-35, with a distinct basal stalk, with basal stalk 7-11 μm long. Paraphyses abundant, intermixed with asci, filamentous, septate, approximately equal in length with asci. Ascospores biseriate within the ascus, 45-53×-10-12 μm, 4-celled, deeply constricted at the septa, end cells with rounded or tapered aspices, middle cells oblong to doliform, each cells with an obscure lateral germ slit, surrounded by a thin, refractive, hyaline sheath, with cells often easily separating, dark olivaceous gray in KOH.

Colonies on potato-dextrose (Difco) agar 10-12 mm in diameter in 7 days at room temperature, slightly raised, about 0.5-1 mm deep, with submerged margin, with surface felty to velutinous, cream when young, soon pale gray to dark gray, or finally dark olivaceous gray to almost black, Cartridge Buff (capitalized color names from Ridgway, R. *Color Standards and Nomenclature*, Washington, D.C. 1912), Marguerite Yellow, Olive Buff, Light Grayish Olive, Grayish olive, Deep Grayish Olive, Iron Gray, Olivaceous Black. In reverse dull yellowish olive to olivaceous gray to dark olivaceous gray. Odors and exudates absent. Often extensive black stromatic regions develop in colonies older than 2-3 weeks. Stromatic regions may contain many embedded, confluent to gregarious pseudothecia.

The culture MF5466, an unidentified bitunicate ascomycete exhibits the following morphological features:

Colonies 10-12 mm in diameter on potato-dextrose agar (Difco) at room temperature, felty, velutinous, smooth to slightly irregular in side view, up to 1 mm deep, with submerged margin, often sectoring into different colony colors, tough to rubbery in texture. Colony margins hyaline to pale, soon pale gray to olivaceous gray, finally dark gray to olivaceous gray, Cream Color, Pale Smoke Gray, Smoke Gray, Light Grayish Olive, Deep Olive Gray, Iron Gray, Olivaceous Black. In some sectors of old cultures, black stomatic tissues with rudimentary pseudothecia or pseudothecia-like structures are formed. Reverse pigmentation similar. Odors and exudates absent. Pigmentation and colony differentiation reduced on nutrient poor media, e.g. cornmeal agar, malt extract agar, dung extract agar. or hay extract agar.

Mycelium septate, highly branched, flexuous, often contorted to nodulose, with elements up to 8 μm in diameter, hyaline to olive or olivaceous gray in KOH. Developing a basal stromatic zone of isodiametic cells in older regions of colonies.

Pseudothecia-like structures up to 400 μm in diameter, dull, black, composed of thin-walled, isodiametric cells and filamentous hyphae, a textura angularis or a combination of *textura angularis* and *textura intricata*, with isodiametric cells up to 8 μm in diameter. Immature bitunicate asci have been observed in some of these rudimentary pseudothecia after 4-6 weeks on oatmeal agar, but cultures become moribund before asci mature.

Compounds of this invention can be obtained by culturing an above noted microorganism in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts and the like. Inorganic nitrogen sources such as ammonium salts (e.g. ammonium nitrate, ammonium sulfate, ammonium phosphate, etc.) can also be use. The various sources of nitrogen can be used alone or in combination in amounts ranging between 0.2 to 90 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organisms which serve as seeds in the production of the active compounds. After inoculation, the flasks are incubated with agitation at temperature ranging from 20° to 30° C., preferably 25° to 28° C. Agitation rates may range up to 400 rpm, preferably 200 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 30 days, preferably 4 to 14 days, with or without agitation (depending on whether liquid or solid fermentation media are employed). The fermentation is conducted aerobically at temperatures ranging from 20° to 40° C. If used, agitation may be at a rate of 200 to 400 rpm. To obtain optimum results, the temperatures are in the range of 22° to 28° C., most preferably 24° to 26° C. The pH of the nutrient medium suitable for producing the active compounds is in the range of 3.5 to 8.5, most preferably 5.0 to 7.5. After the appropriate period for production of the desired compound, fermentation flasks are harvested and the active compound isolated.

A mixture of an alcoholic solvent and an oxygenated solvent, such as an ester or a ketone, is employed to extract a compound of this invention from the solid fermentation medium.

The mixture is vigorously stirred and filtered, and the filtrate is concentrated under reduced pressure. Water is added to the concentrate and the pH is adjusted to about 3 with a mineral acid. The aqueous concentrate is then repeatedly extracted with a water immiscible oxygenated solvent. The water immiscible organic layer is removed and evaporated to dryness. The residue is then generally subjected to several separation steps such as adsorption and partition chromatography, and precipitation. For each separation step, fractions are collected and combined based on results from an assay and/or HPLC/TLC analysis.

The preferred solvent for extraction of the solid fermentation is a 1:1 mixture of methanol and 2-butanone. After concentrating the initial extract and diluting with water, the preferred partitioning solvent is dichloromethane.

The chromatographic separations may be carried out by employing conventional column chromatography with ionic or nonionic resin. Silica gel, such as that available from E. Merck, is the preferred adsorbent. When silica gel is the adsorbent, an alcohol/chlorohydrocarbon/organic acid mixture such as methanol/chloroform/acetic acid/water is useful as an eluant. For reverse phase chromatography, the preferred adsorbent is a C8 bonded phase silica gel. The preferred eluant for reverse phase chromatography is a mixture of acetonitrile and water buffered at a low pH, such as 0.1% phosphoric acid, or trifluoroacetic acid. Ionic resins such as Dowex-1 ($Cl^-$) or Dowex-50 ($Ca^{++}$) are also useful in the purification. The active compound can be precipitated out of a non-polar solvent as the quinine salt. The preferred solvent for precipitation is diethyl ether.

The present invention is also directed to a method of inhibiting cholesterol biosynthesis which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hyperchloesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylene-diamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one, two or all three of the carboxyl groups are in the salt form.

The compounds of this invention may also be coadministered with pharmaceutically acceptable nontoxic cationic polymers capable of binding bile acids in a non-reabsorbable form in the gastro-intestinal tract. Examples of such polymers include cholestyramine, colestipol and poly[methyl-(3-trimethylaminopropyl)imino-trimethylene dihalide]. The relative amounts of the compounds of this invention and these polymers is between 1:100 and 1:15,000.

The intrinsic squalene synthetase inhibitory activity of representative compounds of this invention was measured by the standard in vitro protocol described below:

PREPARATION OF MICROSOMES

Male, Charles River CD rats (120 to 150 g) were fed a diet containing 0.1% lovastatin for 4 days. The livers from these rats were homogenized in 5 volumes (ml/g) of ice cold 50 mM HEPES (4-(2-hydroxyethyl)-1-piperazine-ethanesulfonic acid), 5 mM EDTA (ethylenediaminetetraacetic acid) pH 7.5 with a Potter-Elvehjem type tissue grinder. The homogenate was centrifuged twice at 20,000×g for 15 minutes at 4° C., discarding the pellet each time. The supernatant was then centrifuged at 100,000×g for 1 hour at 4° C. The resulting microsomal pellet was resuspended in a volume of the above homogenizing buffer equal to one-fifth the volume of the original homogenate. This microsomal preparation has a protein concentration of about 7 mg/ml. The microsomal suspensions were stored in aliquots at −70° C. Squalene synthetase activity in these aliquots is stable for at least several months.

Partial Purification of Prenyl Transferase

Prenyl transferase was purified to use in the enzymatic synthesis of radiolabelled farnesyl pyrophosphate. Prenyl transferase was assayed by the method of Rilling (Methods in Enzymology 110, 125–129 (1985)) and a unit of activity is defined as the amount of enzyme that will produce 1 $\mu$mole of farnesyl pyrophosphate per minute at 30° C. in the standard assay.

The livers of 23 forty-day old male rats that had been fed 5% cholestyramine plus 0.1% lovastatin were homogenized in a Waring blender in 1 liter of 10 mM mercaptoethanol, 2 mM EDTA, 25 $\mu$M leupeptin, 0.005% phenylmethyl sulfonyl fluoride pH 7.0 containing 0.1 trypsin inhibitor units of aprotinin/ml. The homogenate was centrifuged at 20,000×g for 20 minutes. The supernatant was adjusted to pH 5.5. with 6N HOAc and centrifuged at 100,000×g for 1 hour. This supernatant was adjusted to pH 7.0 with 3N KOH and a 35–60% ammonium sulfate fraction taken. The 60% pellet was redissolved in 60 ml of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5×5 cm column of DEAE-sepharose 4 B equilibrated with Buffer A. The column was washed with 700 ml of Buffer A and a 1 liter gradient from Buffer A to 100 mM potassium phosphate, 10 mM mercaptoethanol, 1 mM EDTA pH 7.0. Fractions having a specific activity greater than 0.20 units/mg were combined, solid ammonium sulfate was added to bring to 60% saturation and pelleted. The pellet was dissolved in 8 ml of 10 mM Tris, 10 mM $\beta$-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/ml with a specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for at least 6 months.

Enzymatic Synthesis of [4-$^{14}$C]farnesyl-pyrophosphate

The solvent (ethanol: 0.15N NH$_4$OH, 1:1) was removed from 55 $\mu$Ci of [4-$^{14}$C]isopentenyl pyrophosphate (47.9 $\mu$Ci/$\mu$mole) by rotary evaporation. Six hundred microliters of 100 mM Tris, 10 mM MgCl$_2$, 4 mM dithiothreitol pH 7.5 was added and the solution was transferred to a 1.5 ml Eppendorf centrifuge tube. Geranyl-pyrophosphate, 250 $\mu$l of a 20 mM solution, and 50 $\mu$l of the ammonium sulfate suspension of prenyl transferase were added to initiate the reaction. This incubation contained 5 $\mu$moles of geranyl pyrophosphate, 1.15 $\mu$moles of isopentenyl pyrophosphate, 6 $\mu$moles of MgCl$_2$ of 0.18 units of prenyl transferase in a volume of 900 $\mu$l. The incubation was conducted at 37° C. During the incubation, the mix turned cloudy white as the newly formed magnesium complex of farnesyl pyrophoshate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 ml of 50 mM HEPES, 5 mM EDTA, pH 7.5 The yield was 50.7 $\mu$Ci (92%) of [4-$^{14}$C]farnesyl pyrophosphate. The [4-$^{14}$C]farnesyl pyrophosphate was stored in aliquots at −70° C.

Squalene Synthetase Assay

Reactions were performed in 16×125 mm screw cap test tubes. A batch assay mix was prepared from the following solution:

|  | $\mu$l per assay | volume for 50 assays |
|---|---|---|
| 1. 250 mM Hepes pH 7.5 | 20 | 1000 |
| 2. NaF 110 mM | 10 | 500 |
| 3. MgCl$_2$ 55 mM | 10 | 500 |
| 4. Dithiothreitol 30 mM | 10 | 500 |
| 5. NADPH 10 mM (made fresh) | 10 | 500 |
| 6. [4-$^{14}$C]farnesyl-pyrophosphate 47.9 $\mu$Ci/$\mu$mole, and 0.025 $\mu$Ci/3.0 $\mu$l | 3.0 | 150 |
| 7. H$_2$O | 24 | 1200 |

This assay mix was degassed under a vacuum and flushed with N$_2$. Solutions of the squalene synthetase inhibitors were prepared either in DMSO or MeOH and a 1:120 dilution of the microsomal protein was made with the original homogenizing buffer. For each reaction, 87 $\mu$l of the assay mix was taken with 3 $\mu$l of an inhibitor solution (DMSO or MeOH in the controls), warmed to 30° C. in a water bath and then the reaction was initiated by the addition of 10 $\mu$l of the 1:120 dilution of microsomal protein (0.6 $\mu$g protein total in the assay). The reactions were stopped after 20 minutes by the addition of 100 $\mu$l of a 1:1 mix of 40% KOH with 95% EtOH. The stopped mix was heated at 65° C. for 30 minutes, cooled, 10 ml of heptane was added and the mix was vortexed. Two g of activated alumina was then added, the mix vortexed again, the alumina allowed to settle and 5 ml of the heptane layer was removed. Ten ml of scintillation fluid was added to the heptane solution and radioactivity was determined by liquid scintillation counting.

Percent inhibition is caluated by the formula:

$$1 - \frac{[\text{Sample} - \text{Blank}]}{[\text{Control} - \text{Blank}]} \times 100$$

$IC_{50}$ values were determined by plotting the log of the concentration of the test compound versus the percentage inhibition. The $IC_{50}$ is the concentration of inhibitor that gives 50% inhibition as determined from these plots.

Representative of the intrinsic squalene synthetase inhibitory activities of the compounds of this invention are the $IC_{50}$ data tabulated below:

| Compound | Squalene Synthetase $IC_{50}$ |
| --- | --- |
| Compound A | 5 nM |
| Compound B | 5 μM |

The present compounds also demonstrate broad spectrum antifungal activity as determined by broth and agar dilution methods. The compounds are particularly active towards filamentous fungi and yeasts including *Candida albicans* and *Crypt. neoformans*. The sensitivity of filamentous fungi and yeast was determined using inhibitor dilution assays in microtiter format. The compounds were dissolved in DMSO at 2 mg/ml and serially diluted in 0.1M phosphate buffer, pH 7.0 in the microtiter dish from 100 to 0.006 μg/ml. A standardized spore suspension for testing the filamentous fungi was prepared by inoculating Antibiotic Medium #3 containing 1.5% agar with spores such that $1.5 \times 10^3$ colony forming units were added per well. The microtiter wells were filled with 50 μl of buffer containing compound and 50 μl of inoculated medium. The sensitivity of yeasts was determined by inoculating yeast nitrogen base containing 1% dextrose (YNB/G) with aliquots of an overnight yeast culture grown in Yeast Morphology (YM) media at 35° C. and diluting in YNB/G to yield a final concentration of $1.5$–$7.5 \times 10^3$ colony forming units/well. One hundred fifty μl of inoculated media was added per well. To test the sensitivity of yeast, compound was solubilized in 10 percent aqueous DMSO at 2.56 mg/ml. The compound was diluted serially in YNB/G from 128 to 0.06 μg/ml. The wells were filled with 150 μl of drug containing media. The minimum inhibitory concentration (MIC) is defined as the lowest concentration to prevent growth after an incubation for 42 hours, at 28° C. for the filamentous fungi and 24 to 48 hours, at 35° C. for the yeasts. Representative of the antifungal activity are the minimum inhibitory concentration data shown below.

| Minimum Inhibitory Concentration (mcg/ml) | |
| --- | --- |
| Organism | Compound A |
| Filamentous Fungi | |
| *A. fumigatus* MF4839 | 0.098 |
| *A. flavus* MF383 | 0.098 |
| *A. niger* MF442 | 100 |
| *Fus. oxysporum* MF4014 | >100 |
| *Pen. italicum* MF2819 | 0.025 |
| *Coch. miyabeanus* MF4626 | 1.6 |

| -continued | |
| --- | --- |
| Minimum Inhibitory Concentration (mcg/ml) | |
| Organism | Compound A |
| Yeast | |
| *C. albicans* MY1055 | 8 |
| *C. tropicalis* MY1012 | 4 |
| *C. parapsilosis* MY1010 | 4 |
| *Crypt. neoformans* MY1051 | 4 |

Thus the present invention is also directed to a method of treating fungus infections which comprises the administration to an organism in need of such treatment of a nontoxic therapeutically effective amount of a compound represented by the structural formula (I) and pharmaceutically acceptable salts thereof. Based on the above MIC data it is determined that generally from 2 to about 5 mg/kg should be employed as a unit dosage in an antifungal treatment.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals such as man, or birds or reptiles, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of Formula I.

The following examples illustrate the preparation of the compounds of formula (I) and their incorporation into pharmaceutical compositions and, as such, are not to be considered as limiting the invention set forth in the claims appended hereto The preferred route to compound A is Example 2.

The composition of media employed in the following Examples are listed below:

| YME Plating Medium | |
|---|---|
| Component | Amount |
| Yeast Extract | 4.0 g |
| Malt Extract | 10.0 g |
| Glucose | 4.0 g |
| Distilled $H_2O$ | 1000 ml |
| Agar | 25.0 g |

| KF SEED MEDIUM | per liter | Trace Element Mix | g/L |
|---|---|---|---|
| Corn Steep Liquor | 5 g | $FeSO_4.7H_2O$ | 1.0 |
| Tomato Paste | 40 g | $MnSO_4.4H_2O$ | 1.0 |
| Oat Flour | 10 g | $CuCl_2.2H_2O$ | 0.025 |
| Glucose | 10 g | $CaCl_2.2H_2O$ | 0.1 |
| Trace Element Mix | 10 ml | $H_3BO_3$ | 0.056 |
| | | $(NH_4)_6Mo_7O_{24}.4H_2O$ | 0.019 |
| pH adjusted to 6.8 (presterile) | | $ZnSO_4.7H_2O$ | 0.2 |
| 50 mls/nonbaffled 250 mls Erlenmeyer flask | | dissolved in 1 L 0.6 N HCl | |
| autoclave 20 minutes (121° C., 15 psi) | | | |

| Production Media | | | |
|---|---|---|---|
| F204 | | BRF | |
| Millet | 15.0 g/flask | Brown rice | 5.0 g/flask |
| Base liquid #1 | 10.0 mls/flask | Base liquid #2 | 20.0 mls/flask |
| Base liquid #1 | g/L | Base liquid #2 | g/L |
| Yeast extract | 50.0 | Yeast extract | 1.0 |
| Monosodium glutamate | 10.0 | Sodium tartrate | 0.5 |
| Corn oil | 10.0 mls | $KH_2PO_4$ | 0.5 |
| Sodium tartrate | 10.0 | distilled water | 1000.0 mls |
| $FeSO_4.7H_2O$ | 1.0 | | |
| distilled water | 1000.0 mls | (no pH adjustment) | |
| (no pH adjustment) | | autoclave 15 minutes (121° C., 15 psi) | |
| | | add 15.0 mls distilled $H_2O$/flask | |
| autoclave 15 minutes (121° C., 15 psi) | | autoclave 20 minutes (121° C., 15 psi) | |
| add 15.0 mls distilled $H_2O$/flask | | | |
| autoclave 20 minutes (121° C., 15 psi) | | | |

EXAMPLE 1

Preparation of Compound A

A. Culturing MF5447

Culture MF5447, inoculated from a soil tube using one glass scoop of soil, was grown in KF seed medium for 72 hours at 25° C., 220 rpm, 85% humidity. At the end of this incubation period, 2.0 mls aliquots were aseptically transferred to each of 45 F204 250 ml Erlenmeyer production flasks. Production flasks were incubated at 25° C. statically for 21 days and then harvested. At harvest 40 mls of methyl ethyl ketone were added to each flask and the solid growth was manually broken apart into smaller pieces. Flasks were then placed onto a gyrotory shaker and shaken at 220 rpm for 30 minutes in order to further break up the mycelial mass as well as to improve contact of the solvent with the cells. After shaking, the contents of the individual flasks were pooled by pouring the entire contents of the flasks (solids and all) into a 4 L beaker.

B. Isolation of Compound A

The methyl ethyl ketone liquid from approximately 2 liters of fermentation extract, cultured for 21 days as described in Example 1A was filtered off. A mixture of ethyl acetate and methanol (1:1, 2 L) was then added to the solid residue. This was stirred for 18 hours using a mechanical stirrer. The mixture was filtered and the filtrate concentrated (Rotovap; 40° C.) to approximately 700 mL. Ethyl acetate (700 mL) was added followed by 500 mL of 5% sodium chloride/water. After stirring for 15 minutes, the aqueous layer was removed and discarded. The ethyl acetate layer was concentrated (Rotovap; 40° C.) to approximately 150 mL. Hexane (500 mL) and methanol (500 mL) were added and the mixture stirred for 15 minutes. The hexane layer was removed and discarded. The methanol layer was dried (Rotovap; 40° C.) to afford a crude extract.

The crude extract (1.4 g) was dissolved in 25 mL of 3:1:1 hexane/toluene/methanol and applied to a Sephadex LH-20 chromatography column (1 L resin) eluting with the same solvent mixture and with a flow rate approximately 3 mL/minute. The first 1600 mL of eluant was discarded. The following 3600 mL eluant was concentrated to dryness to afford LH-20 eluate. Approximately 310 mg of the LH-20 Eluate was dissolved in 5 mL of 5% methanol/chloroform. This was applied to a silica gel chromatography column (50 mL of E. Merck Kieselgel 40–63 um). The column was eluted stepwise as shown in Table 1a below. Fractions 4–6 were combined and dried to afford an oily residue. The residue (115 mg) was dissolved in 4 mL of tetrahydrofuran and 5 mL of 0.005N hydrochloric acid was added. The resulting suspension was centrifuged (10,000 rpm; 20 minutes). The supernatant was removed and discarded to yield a precipitate.

Twenty-four milligram of this precipitate was dissolved in 0.2 mL of tetrahydrofuran and 0.2 mL of dimethylsulfoxide was added. This was then adsorbed on the resin bed of an open RP-18 chromatography column (30 mL of Bakerbond 40 μm RP-18), equilibrated with 10% tetrahydrofuran/water. Stepwise elution (Table 1b below) was followed by HPLC analysis and bioassay of the fractions. Fractions 2–7 were combined and concentrated to approximately 50 mL. The aqueous solution was extracted with 50 mL of ethyl acetate. The ethyl acetate extract was dried and dissolved in 0.3 mL of methanol, followed by the addition of 0.4 mL dimethylsulfoxide, 0.1 mL water, and 0.05 mL 43% acetonitrile/10 mM potassium phosphate buffer (pH 7). This solution was injected on an HPLC column (Amicon Matrex Silica MC-100A C8 15 um, 4.6 mm ID×25 cm) eluting with 43% acetonitrile/10 mM potassium phosphate buffer (pH 7) at 1 mL/minute. Fractions 9–12 were combined and 0.05 mL of 0.5N hydrochloric acid was added, followed by 10 mL of ethyl acetate. The ethyl acetate layer was dried to afford Compound A.

TABLE 1a

Solvent composition for silica gel chromatography of the LH-20 Eluate.

| Fraction | Solvent % (methanol/water/acetic acid 10:1:1) in chloroform | Volume |
|---|---|---|
| 1 | 5 | 50 mL/fraction |
| 2–3 | 10 | 50 mL/fraction |
| 4–5 | 20 | 50 mL/fraction |
| 6–7 | 30 | 50 mL/fraction |
| 8–9 | 50 | 50 mL/fraction |
| 10–11 | 75 | 50 mL/fraction |
| 12 | 100 | 50 mL/fraction |

TABLE 1b

Solvent composition for chromatography of the precipitate on Bakerbond RP-18.

| Fraction | Solvent % tetrahydrofuran in water | Volume |
|---|---|---|
| 1 | 10 | 25 mL/fraction |
| 2–3 | 25 | 25 mL/fraction |
| 4–5 | 50 | 25 mL/fraction |
| 6–7 | 75 | 25 mL/fraction |
| 8 | 100 | 25 mL/fraction |

EXAMPLE 2

Preparation of Compound A

A. Culturing MF5447

Fermentation procedures were identical to those in Example 1A except that 23 F204 flasks were inoculated and the fermentation time was 14 days. 50 mls of methanol was added to each flask, then growth was manually broken up and flasks shaken as stated in Example 1A. Contents of the flask were pooled by pouring the entire contents into a 3 L beaker.

B. Isolation of Compound A

Approximately 2 liters of a fermentation extract cultured for 14 days as described in Example 2A and containing an additional one liter of methanol was vigorously stirred for 16 hours and filtered. A second 1 L portion of methanol was added to the spent solids, stirred for 4 hours and filtered. The methanol extracts were combined and concentrated (rotovap, 47° C.) to approximately 200 mL. Water (300 mL) was added to the concentrate and the pH was adjusted to 3 with hydrochloric acid. n-Butanol (500 mL) was added and stirred for 20 minutes. The organic layer was removed and evaporated to dryness to give a black tar. This was chromatographed (2.9 g) on silica gel in a fashion similar to that described in Examples 1 and 3. Fractions containing Compound A (from HPLC analysis results) were combined and evaporated to dryness (rotovap, 40° C.). The oily residue (230 mg) was dissolved in 1 mL of dimethyl sulfoxide and injected on an HPLC column (DYNAMAX 60A 8 micron C8; 21.4 mm ID×25 cm with guard module) eluting with the solvent gradient shown in Table 2a with a flow rate of 10 mL/minute. Collecting 5 mL fractions, fractions 37–42 were combined. Ethyl acetate (50 mL) and water (50 mL) were added. After extraction, the ethyl acetate layer was separated and dried (Rotovap, 40° C.) to afford Compound A.

TABLE 2a

Solvent Gradient for HPLC Preparative Purification of Silica Gel Rich Cut.

| Time (min) | Solvent % acetonitrile in 0.1% $H_3PO_4$/water |
|---|---|
| 0–10 | 70%, isocratic |
| 10–20 | 70–90%, linear gradient |
| 20–30 | 90%, isocratic |

| Analytical HPLC system: | |
|---|---|
| column: | Dynamax-60A 8 micron C8, 4.6 mm ID × 25 cm with guard (1.5 cm L) |
| eluent: | 80:20 acetonitrile/0.1% phosphoric acid in water |
| flow rate: | 1.0 mL/minutes |
| detection: | UV at 250 nm |
| retention time of Compound A: | 5.52 minutes |

EXAMPLE 3

Preparation of Compound A

A. Culturing MF5466

Culture MF5466 was grown on a YME slant at 25° C. for at least two weeks. One-fifth of the growth on the slant was transferred to a seed flask containing 54 mL of KF medium in a 250 mL unbaffled Erlenmeyer flask. The seed flask was then incubated for 72 hours at 24° C., 220 rpm. At the end of this incubation, 2 mL aliquots were transferred into multiple 250 ml Erlenmeyer production flasks containing F204 medium. Production flasks were then incubated stationary at 24° C. for 21 days. At harvest, 50 mL of 70% methanol was added to the production flasks and mycelial growth was broken apart manually with a pipet. The flasks were shaken at 220 rpm for 30 minutes. The methanol extracts were pooled, filtered and the residues were combined.

B. Isolation of Compound A

The combined solids formed as described in Example 3A, were extracted vigorously with 1 L of methanol for 15 hours. The 1 L extract was concentrated to 250 ml, diluted with an equal volume of water, adjusted to pH 8.5 and extracted with 500 ml of isopropyl acetate. The aqueous solution was then acidified to pH 4.0 and successively extracted twice with ethyl acetate and once with 1-butanol. Each extract was individually concentrated to 40 ml (Ethyl Acetate Extract 1, Ethyl Acetate Extract 2, Butanol Extract 1).

A 20 ml aliquot of Ethyl Acetate Extract 1 (250 mg total solids) was concentrated to dryness and reconstituted in 5 ml of 93/4/1/2 chloroform-methanol-water-acetic acid. The sample was charged to a 10 ml column of silica gel 60 which had been equilibrated in the same solvent. The column was then eluted stepwise (see Table 3a).

TABLE 3a

Solvent Composition (by volume) for Silica Gel Chromatography of Crude EtOAc Extract.

| Fraction | CHCl$_3$ | CH$_3$OH | H$_2$O | CH$_3$COOH |
|---|---|---|---|---|
| 1-8 | 93 | 4 | 1 | 2 |
| 9-16 | 89 | 8 | 1 | 2 |
| 17-24 | 85 | 12 | 1 | 2 |
| 25-32 | 78 | 18 | 2 | 2 |
| 33-38 | 59 | 33 | 4 | 4 |

The volume of all fractions was 5 ml each. Fractions 18-28 were combined and concentrated to dryness. The residue (40 mg total solids) was dissolved in 4 ml of tetrahydrofuran, to which was added with stirring 5 ml of water. The resulting cloudy mixture was centrifuged for 20 minutes at 15000 rpm. An oily precipitate (ppt 1) was formed and collected.

Ethyl Acetate Extract 2 (40 mL) and the remainder of Ethyl Acetate Extract 1 (20 mL) were processed in a similar fashion through the silica gel and precipitation steps to give an oily precipitate (ppt 2). The two precipitates were combined (43 mg) and dissolved in 0.5 mL of dimethyl sulfoxide and 0.5 mL of methanol. The solution was injected on an HPLC column (DYNAMAX 60A 8 micron C8; 21.4 mm ID×25 cm with guard module) eluting with the solvent gradient shown in Table 3b and with a flow rate of 10 mL/minute. Collecting 5 mL fractions, fractions 21-36 were combined. Ethyl acetate (100 mL) was added and the pH of the aqueous phase was adjusted to 3 with hydrochloric acid. After extraction, the ethyl acetate layer was dried (Rotovap, 40° C.) to afford Compound A.

TABLE 3b

Solvent Composition of Gradient for HPLC Purification of Precipitate.

| Time (min) | Solvent % acetonitrile in 10 mM Potassium phosphate buffer (pH 7) |
|---|---|
| 0-15 | 42%, isocratic |
| 15-20 | 42-70%, linear gradient |
| 20-30 | 70%, isocratic |

EXAMPLE 4

As a specific embodiment of an oral composition of a compound of this invention, 20 mg of the compound from Example 1 is formulated with sufficient finely divided lactose to provide a total amount of 580 to 590 mg to fill a size 0 hard gelatin capsule.

EXAMPLE 5

Preparation of an Ammonium Salt

A 0.1 mmol sample of the free acid of a compound of formula (I) is dissolved in 10 ml of ethyl acetate. The resulting solution is saturated with gaseous ammonia upon which the ammonium salt precipitates from solution.

EXAMPLE 6

Preparation of a Potassium Salt

A solution of 0.1 mmol of the free acid of a compound of formula (I) in 10 ml of methanol is treated with an aqueous or methanolic solution containing 0.3 mmol of potassium hydroxide. Evaporation of the solvent affords the tri-potassium salt. Addition of between 0.1 and 0.3 mmol of potassium hydroxide yields analogously mixtures of the mono-potassium, di-potassium and tri-potassium salts whose composition depends upon the exact amount of potassium hydroxide added.

In a similar fashion the sodium and lithium salts can be formed.

EXAMPLE 7

Preparation of a Calcium Salt

A solution of 0.1 mmol of the free acid of a compound of formula (I) in 20 ml of 6:4 methanol/water is treated with an aqueous solution of 0.1 mmol of calcium hydroxide. The solvents are evaporated to give the corresponding calcium salt.

EXAMPLE 8

Preparation of an Ethylenediamine Salt

A solution of 0.1 mmol of the free acid of a compound of formula (I) in 10 ml of methanol is treated with 0.1 mmol of ethylenediamine. Evaporation of the solvent affords the ethylenediamine salt.

The procedure can also be applied to the preparation of the N,N''-dibenzylethylenediamine salt.

EXAMPLE 9

Preparation of a Tris(hydroxymethyl)aminomethane Salt

To a solution of 0.1 mmol of the free acid of a compound of formula (I) in 10 ml of methanol is added from 0.1 to 0.3 mmol of tris(hydroxymethyl)aminomethane dissolved in 10 ml of methanol. Evaporation of the solvent gives a corresponding salt form of the exact composition of which is determined by the molar ratio of amine added. Similarly prepared are the salts of L-ornithine, L-lysine, and N-methylgluacamine.

EXAMPLE 10

Preparation of an L-arginine Salt

A solution of 0.1 mmol of the free acid of a compound of formula (I) in 10 ml of 6:4 methanol/water is treated with an aqueous solution of 0.1 to 0.3 mmol of L-arginine. Evaporation of the solvent affords the title salt, the exact composition of which is determined by the molar ratio of amino acid to the free acid of formula (I) used.

Similarly prepared are the salts of L-orinithine, L-lysine and N-methylglucamine.

EXAMPLE 11

Preparation of a Compound B (Method 1)

A solution of 2 mg of Compound A in 5 ml of methanol/ether (1:1) was treated with a slight excess of ethereal diazomethane. After 5 minutes excess diazomethane was removed and the solvent was evaporated to give Compound B.

EXAMPLE 12

Preparation of Compound B (Method 2)

A solution of 2 mg of Compound A in 0.5 ml of acetonitrile is treated at room temperature with 10 equivalents of DBU and 10 equivalents of MeI. After 2 hours the reaction is diluted with 10 ml of dichloromethane and washed successively with 10 ml of 0.1 M phosphoric acid, 10 ml of water, 10 ml of saturated sodium bicarbonate and 10 ml of water. After drying over sodium sulfate, the organic layer is concentrated and the residue is chromatographed on silica gel using mixtures of hexane and ethyl acetate to give Compound B.

The method of Example 12 is also suitable for the preparation of other ester derivatives such as 1) ethyl and other lower alkyl esters and 2) benzyl and substituted benzyl esters.

Mass Spectral Data

Mass spectra were recorded on Finnigan-MAT model MAT212 (electron impact, EI, 90 eV), MAT 90 (Fast Atom Bombardment, FAB), and TSQ70B (FAB, EI) mass spectrometers. Exact mass measurements were performed at high resolution (HR-EI) using perfluorokerosene (PFK) or perfluoropolypropylene oxide (Ultramark U1600F) as internal standard. Trimethylsilyl derivatives were prepared with a 1:1 mixture of BSTFA-pyridine at room temperature.

$^{13}$C NMR Data

The $^{13}$C NMR spectrum of Compound A was recorded in CD$_3$OD at 100 MHz on a Varian XL400 spectrometer. Chemical shifts are given in ppm relative to tetramethylsilane (TMS) at zero ppm using the solvent peak at 49.0 ppm as internal standard.

$^1$H NMR Spectra

The $^1$H NMR spectra were recorded at 400 MHz in CD$_3$OD and C$_6$D$_6$ on a Varian XL400 spectrometer. Chemical shifts are shown in ppm relative to TMS at zero ppm using the solvent peaks at 3.30 ppm (CD$_3$OD) and 7.15 ppm (C$_6$D$_6$) as internal standards.

Physical Properties of the compounds of Structure I

Compound A-the compound of structure (I) wherein Z$_1$ Z$_2$ and Z$_3$ are each hydrogen.

Mass Spectral Data

This compound has the molecular weight 730 by FAB-MS (observed [M+H]$^+$ at m/z 731, and with addition of lithium acetate [M·Li$_3$+Li]$^+$ (i.e., the lithium adduct of the trilithium salt at m/z 755). The molecular formula C$_{39}$H$_{54}$O$_{13}$ was determined by HR-EI measurement of the hexa-trimethylsilyl derivative (calc for C$_{39}$H$_{54}$O$_{13}$+(SiC$_3$H$_8$)$_6$—CH$_3$ 1147.5701, found 1147.5751).

Figure 1:
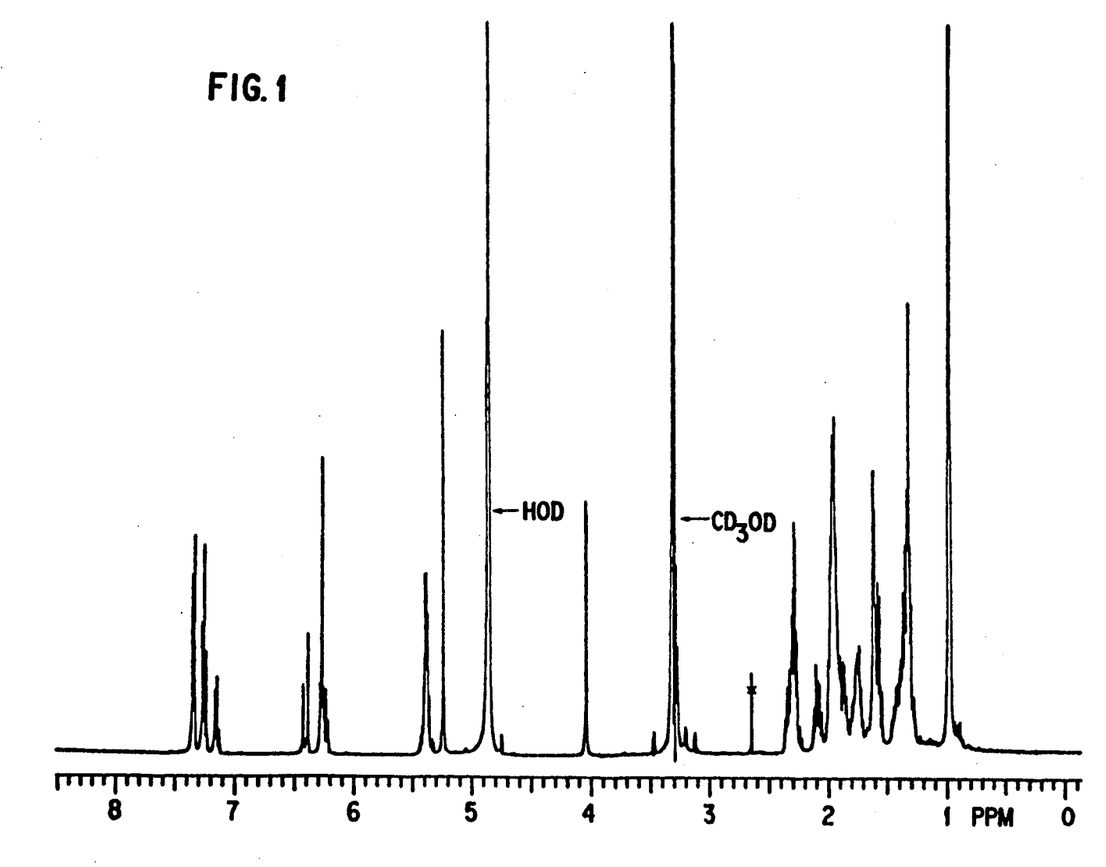

$^1$H NMR spectrum (400 MHz) (CD$_3$OD, 22° C.): See FIG. 1.

$^{13}$C NMR Chemical Shifts (CD$_3$OD, 22° C.): 14.8, 15.2, 18.1, 25.3, 27.5, 30.1, 30.3 (2x), 33.2, 33.5 (2x), 33.9, 34.8, 36.7, 36.9, 38.6, 75.7, 76.7, 78.4, 81.0, 82.0, 91,1, 107.5, 125.7, 127.0 (2x), 127.9, 129.5 (2x), 130.2, 131.0, 131.9, 132.57, 132.63, 139.3, 168.6, 170.3, 172.6, 173.6 ppm.

UV (MeOH): λ max is 250 nm (ε23,000) IR (as free acid; film on ZnSe): 3220 br, 2924, 2855, 2489 br, 1741, 1436, 1417, 1266, 1152, 1122, 1004, 967, 950, 804, 744, 695 cm$^{-1}$.

Compound B-the trimethyl ester of Compound A, i.e. the compound of structure (I) wherein Z$_1$, Z$_2$ and Z$_3$ are each methyl.

Mass Spectral Data:

This compound has the molecular weight 772 by FAB-MS (observed [M+Li]$^+$ at m/z 779 in the lithiated spectrum). The molecular formula C$_{42}$H$_{60}$O$_{13}$ was determined by HR-EI measurement of the tris-trimethylsilyl derivative (calc for C$_{42}$H$_{60}$O$_{13}$+(SiC$_3$H$_8$)$_3$ 988.5220, found 988.5172).

Figure 2:
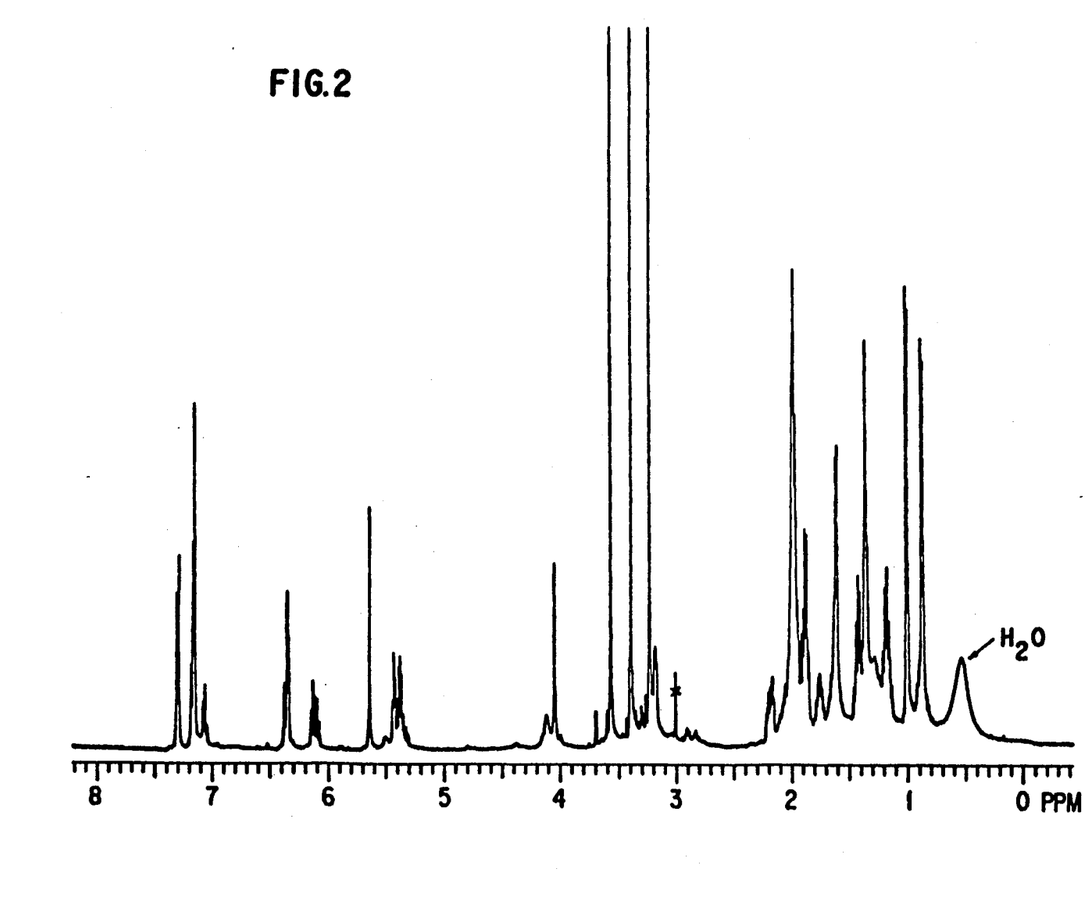

$^1$H NMR Spectrum (400 MHz) (C$_6$D$_6$, 22° C.): See FIG. 2.

What is claimed is:

1. A compound of structural formula (I)

wherein
Z$_1$ Z$_2$ and Z$_3$ are each independently selected from
a) H;
b) C$_{1-5}$ alkyl;
C$_{1-5}$ alkyl substituted with a member of the group consisting of
 i) phenyl,
 ii) phenyl substituted with methyl, methoxy, halogen (Cl, Br, I, F) or hydroxy; or
a pharmaceutically acceptable salt of a compound of formula (I) in which at least one of Z$_1$, Z$_2$ and Z$_3$ is hydrogen.

2. A compound of claim 1 wherein the relative configuration of structural formula (I) is:

3. A compound of claim 2 wherein the relative configuration within structural formula (I) is:

4. A compound of claim 3 wherein the relative configuration of structural formula (I) is:

5. A compound of claim 4 in which $Z_1$, $Z_2$ and $Z_3$ are each hydrogen or a pharmaceutically acceptable salt thereof.

6. A compound of claim 4 in which $Z_1$, $Z_2$ and $Z_3$ are each methyl.

7. A compound of claim 1 which is:

8. A pharmaceutical composition comprising a nontoxic therapeutically effective amount of a compound of claim 1 and a pharmaceutically acceptable carrier.

9. A composition of claim 8 wherein the therapeutically effective compound is selected from the group consisting of:

10. A pharmaceutical composition comprising a nontoxic therapeutically effective amount of a compound of claim 1 in combination with a pharmaceutically acceptable nontoxic cationic polymer capable of binding bile acids in a non-reabsorbable form in the gastrointestinal tract and a pharmaceutically acceptable carrier.

11. A method of treating hypercholesterolemia comprising the administration to a subject in need of such treatment a nontoxic therapeutically effective amount of a compound of claim 1.

12. A method of claim 11 wherein the therapeutically effective compound is selected from the group consisting of:

and;

13. A method of inhibiting squalene synthetase comprising the administration to a subject in need of such treatment a nontoxic therapeutically effective amount of a compound of claim 1.

14. A method of claim 13 wherein the therapeutically effective compound is selected from:

* * * * *